(12) United States Patent
Ronn

(10) Patent No.: US 8,014,003 B2
(45) Date of Patent: Sep. 6, 2011

(54) BODY METRIC DIFFERENTIAL MEASUREMENT DEVICE

(75) Inventor: Avigdor Ronn, Great Neck, NY (US)

(73) Assignee: Avigdor Ronn, Great Neck, NY (US)

( * ) Notice: Subject to any disclaimer, the term of this patent is extended or adjusted under 35 U.S.C. 154(b) by 420 days.

(21) Appl. No.: 12/321,540

(22) Filed: Jan. 22, 2009

(65) Prior Publication Data

US 2009/0190140 A1    Jul. 30, 2009

Related U.S. Application Data

(60) Provisional application No. 61/062,451, filed on Jan. 26, 2008.

(51) Int. Cl.
*G01N 11/14* (2006.01)
(52) U.S. Cl. ....................................................... 356/614
(58) Field of Classification Search ........... 356/600–640
See application file for complete search history.

(56) References Cited

U.S. PATENT DOCUMENTS

| | | | | |
|---|---|---|---|---|
| 4,328,620 A * | 5/1982 | Mack et al. | | 33/514 |
| 4,530,367 A * | 7/1985 | Desjardins et al. | | 600/590 |
| 4,649,504 A * | 3/1987 | Krouglicof et al. | | 702/153 |
| 4,694,478 A * | 9/1987 | Delnon | | 378/39 |
| 5,203,091 A * | 4/1993 | Al-Farsy | | 33/558.3 |
| 5,402,585 A * | 4/1995 | Lund | | 33/832 |
| 5,462,065 A * | 10/1995 | Cusimano | | 600/595 |
| 6,110,130 A * | 8/2000 | Kramer | | 600/595 |
| 6,304,840 B1 * | 10/2001 | Vance et al. | | 703/21 |
| 6,820,025 B2 * | 11/2004 | Bachmann et al. | | 702/94 |
| 7,402,996 B2 * | 7/2008 | Arai et al. | | 324/207.17 |
| 7,565,295 B1 * | 7/2009 | Hernandez-Rebollar | | 704/271 |

* cited by examiner

*Primary Examiner* — Gregory J Toatley
*Assistant Examiner* — Jarreas C Underwood

(57) ABSTRACT

A method of measuring a metric of a measurement area of interest on a subject comprises contacting a part of the subject on a rest of a measurement apparatus that comprises an arm, a base attached to or formed on the arm, and a displacement sensor attached to the arm; adjusting the measurement apparatus to optimize the spatial relationship between the displacement sensor and the measurement area of interest on the subject; and measuring the metric.

16 Claims, 5 Drawing Sheets

BODY METRIC DIFFERENTIAL MEASUREMENT DEVICE

This application claims the benefit of U.S. Patent Application No. 61/062,451 filed Jan. 26, 2008.

BACKGROUND OF THE INVENTION

The present invention is directed to a device useful for measuring a movement metric of a body. Specifically, the present is directed to a device useful for measuring a difference in a movement metric of a body.

There is a need to measure efficiently, precisely, easily, and reproducibly differences in bodily movement—particularly in the physical therapy area. Progress in physical therapy treatments from one session to the next can be subtle, with very little discernable changes. Nevertheless, a record of any changes, improvement or not, is important for reasons such as tracking efficacy of treatment modalities, alerting of any change in physical condition, and reporting any need for further treatments. Additionally, treatment reimbursements may depend on a showing of impairment and improvement. Further, for the patient, any such seemingly lack of improvement can be discouraging and may lead to noncompliance to treatment protocols. Thus, there is a need for a device useful for measuring a movement metric of a body.

One out of every seventeen people has difficulty swallowing (dysphagia). Thus, this condition affects 6 to 10 million people in the U.S. alone. Of these, approximately only a few hundred are hospital patients, fewer than a thousand are nursing home patients, while approximately a third are rehabilitation patients. The most common outcome of dysphagia is aspiration pneumonia, which has estimated costs of $19,000 per patient with a national cost exceeding $3 billion per year.

While there are a number of treatment protocols and methods that are used by speech and physical therapists to assist in correcting this debilitating condition, there is no reliable, objective, and non-invasive method that allows the practitioner to gauge the patient's therapeutic progress. Accordingly, there is a need for a reliable, simple, non-invasive method and device to measure the therapeutic progress of such patients.

SUMMARY OF THE INVENTION

A method of measuring a metric of a measurement area of interest on a subject comprises contacting a part of the subject on a rest of a measurement apparatus that comprises an arm, a base attached to or formed on the arm, a rest attached to or formed on the arm, and a displacement sensor attached to the arm; adjusting the measurement apparatus to optimize the spatial relationship between the displacement sensor and the measurement area of interest on the subject; and measuring the metric.

A method of measuring a metric of a measurement area of interest on a subject comprises contacting a part of the subject on a rest of a measurement apparatus that comprises a base, an arm assembly lockably adjustably connected to the base, a rest adjustably lockably connected to the arm assembly, and a displacement sensor lockably adjustably attached to the arm assembly; adjusting the measurement apparatus to optimize the spatial relationship between the displacement sensor and the measurement area of interest on the subject; locking the measurement apparatus in such relationship; and measuring the metric.

A device of this invention for measuring a metric of a measurement area of interest on a subject comprises an arm, a rest attached to or formed on the arm, a base attached to or formed on the arm; and a displacement sensor attached to the arm; wherein the arm, rest, and displacement sensor can be adjusted to optimize the spatial relationship between the displacement sensor and the measurement area of interest on the subject.

A measurement apparatus for measuring a metric of a measurement area of interest on a subject comprises an arm; a rest attached to or formed on the arm; a base attached to or formed on the arm; and a displacement sensor attached to the arm; wherein the arm, rest, and displacement sensor can be adjusted to optimize the spatial relationship between the displacement sensor and the measurement area of interest on the subject.

DETAILED DESCRIPTION OF THE INVENTION

Figure 1:
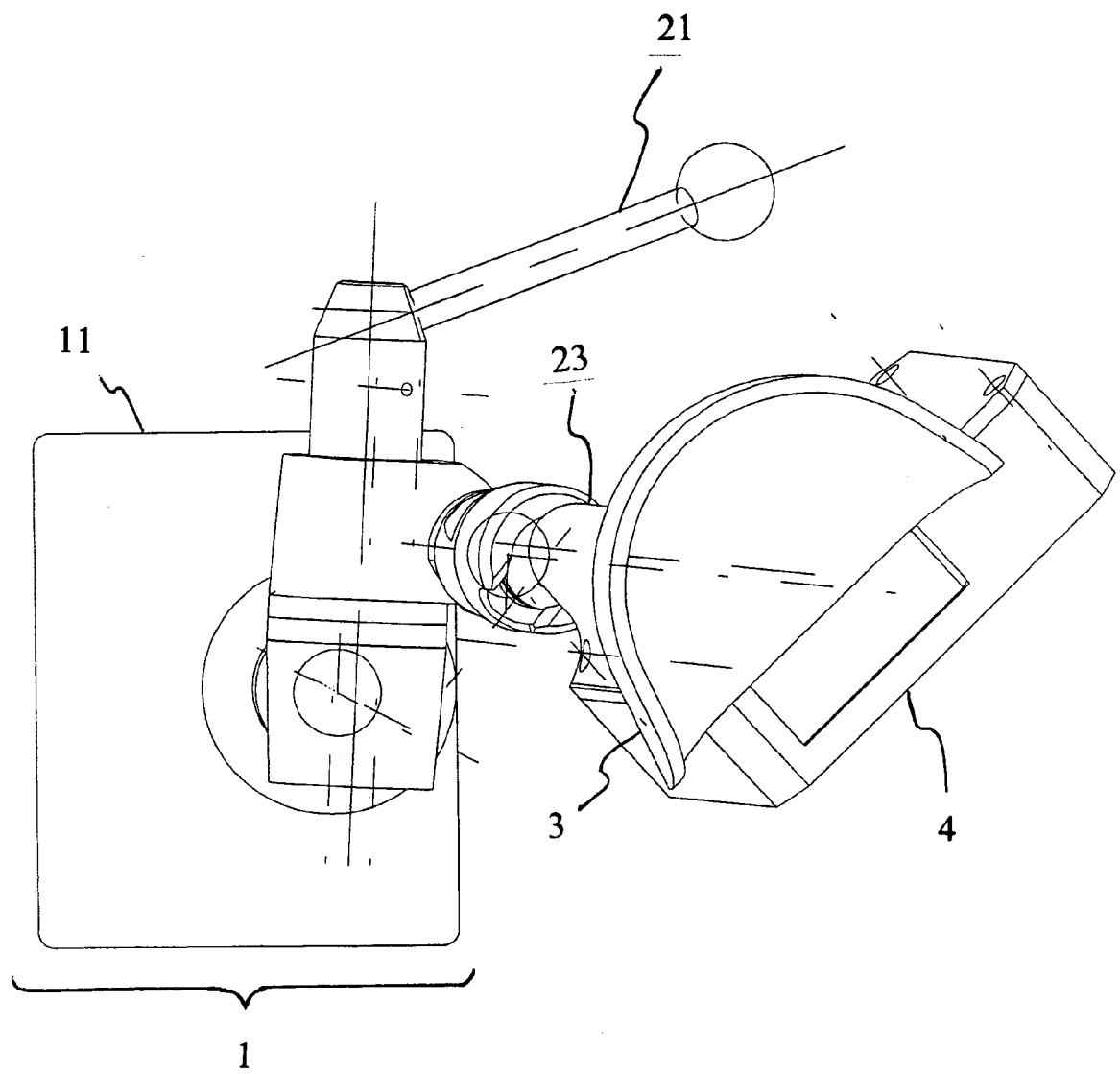
FIG. 1 is a perspective drawing of an embodiment of the present invention.
Figure 2:
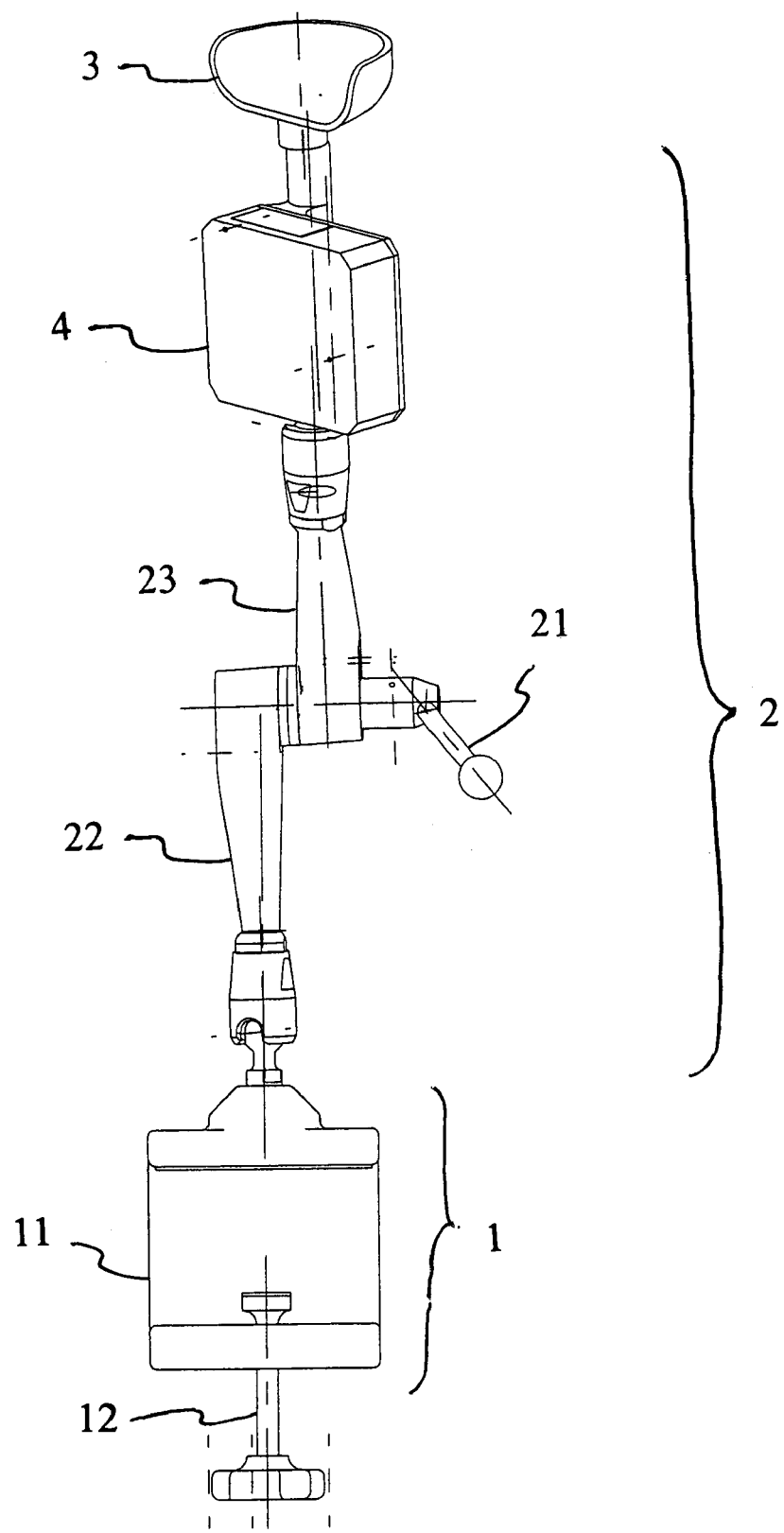
FIG. 2 is a perspective drawing of an embodiment of the present invention.
Figure 3:
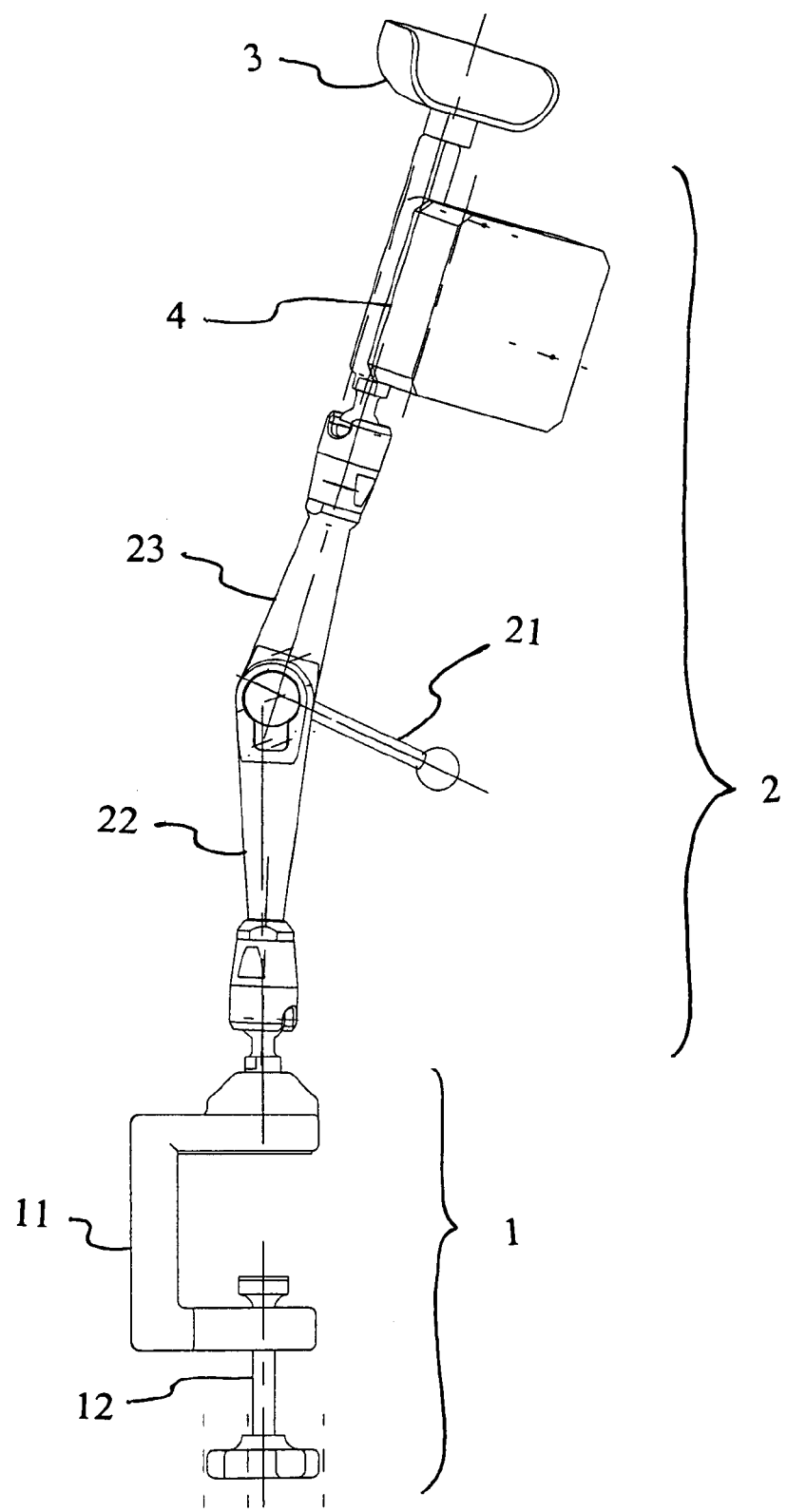
FIG. 3 is a perspective drawing of an embodiment of the present invention.
Figure 4:
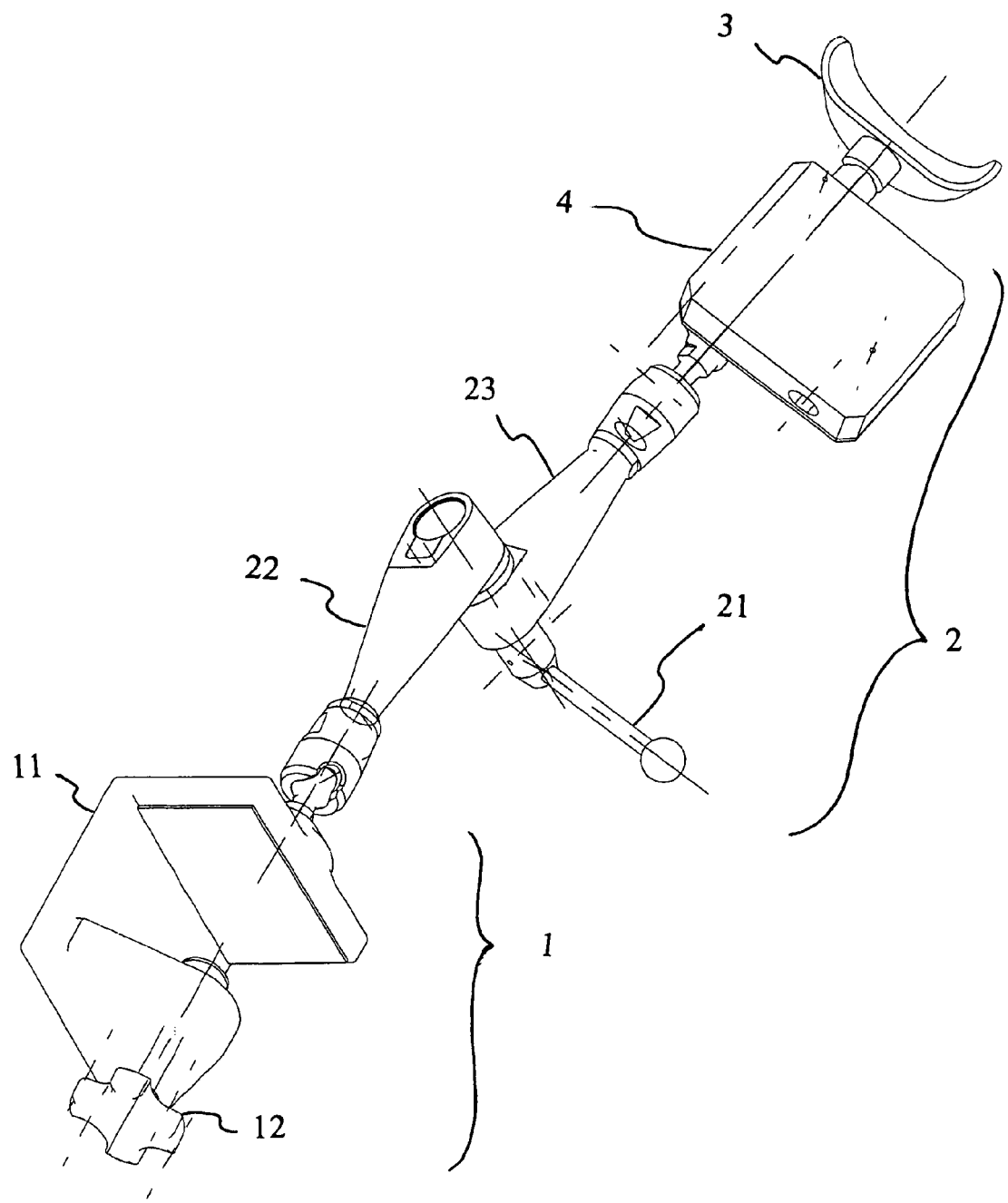
FIG. 4 is a perspective drawing of an embodiment of the present invention.

The device of the present invention relies on the application of an extremely accurate displacement measurement of the external muscle groups involved in swallowing. It accomplishes this accuracy without contact to any of the patient's muscles by utilizing an external laser displacement sensor.

The act of swallowing generates a visible movement in the external laryngeal/phyrangial region. In normal swallowing people, this range of motion is typically 1-4 cm. In dysphagia patients, the range of this motion is severely curtailed. The success of a typical dysphagic patient's rehabilitation generally relies on the therapist's ability to gauge the patient's swallowing efficiency via a subjective observation of this motion, aided by the patient's own assessment of her ability to swallow a variety of test "foods". This method of patient assessment is slow as it requires a one-on-one interaction with a skilled therapist each time. Further, the method is subjective thereby requiring repeated visits to the same provider.

Such subjective measurements also make it difficult to develop a national standard for therapeutic success or failure. As new therapeutic modalities for the treatment of dysphasia are being developed and tested by the rehabilitation community, the need for national standards is becoming increasingly important as evidenced by the large number of papers on the subject at the Dysphagia Research Society Meeting in October 2003.

The present invention incorporates the well known technology of laser based displacement sensing, long available in many industrial settings, into a small table top design, which may be portable, that allows the measurement of muscular displacement with exceptional accuracy and precision rapidly and non-invasively. Such laser displacement sensors are available from, for example, Acuity Research, Menlo Park, Calif. (Model AccuRange 200).

The laser displacement sensor projects a beam of light of a visible wavelength that creates a spot on the target surface. Reflected light from that surface is viewed at an angle by a line camera inside the sensor. The target's distance is computed from the image pixel data. Tests on dysphagia patients show that the sensor successfully measured muscle movement on a subject's throat with an accuracy of better than 1 mm in muscle displacement.

The present invention, in another aspect, incorporates the well known technology of fiberoptic based displacement sensing into a small table top design, which may be portable, that allows the measurement of muscular displacement with exceptional accuracy and precision rapidly and non-invasively. Such fiberoptic displacement sensors, for example, are available from Philtec, Inc., Annapolis, Md.

The fiberoptic displacement sensor projects a beam of light of a visible wavelength (from an light emitting diode LED or a semiconductor laser, for example) that creates a spot on the target surface. Reflected light from that surface is viewed at an angle by a line camera inside the sensor. The target's distance is computed from the image pixel data. Tests on dysphagia patients show that the sensor successfully measured muscle movement on a subject's throat with an accuracy of better than 1 mm in muscle displacement.

In addition to the displacement sensor, the device of the present invention includes a power supply effective to power the displacement sensor, cables effective to lead power to the displacement sensor, and a display panel that shows the measurement data. Further, the device of the present invention includes a base. The device includes an arm effective to hold a rest in steady alignment with the base during a measurement. The rest is effective to hold the measurement subject's metric area steady relative to the displacement sensor, which is conveniently mounted on the arm.

Referring to FIGS. 1-4, in one embodiment, base (1) comprises a bracket (11) with a turnscrew (12) effective to mount the device on, for example, the edge of a desk stably. Arm assembly (2) comprises a single locking multilinkage that conveniently loosens by turning locking lever (21) to enable lower arm (22) and upper arm (23) to pivot freely to place rest (3) at a convenient location, at which time lever (21) is turned to lock the entire assembly. Displacement sensor (4) is conveniently mounted on arm (2) effective to measure the area of interest on the subject.

Figure 5:
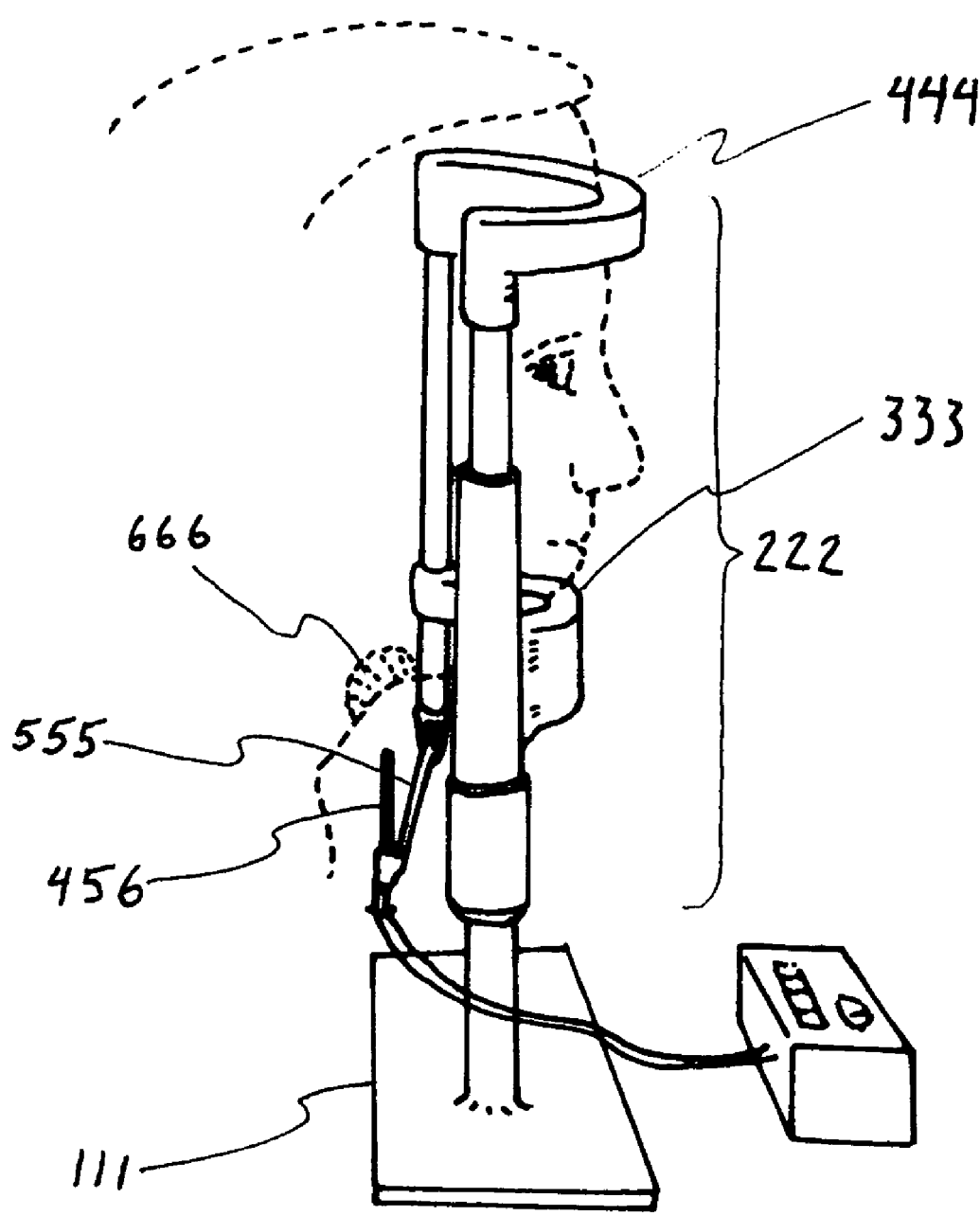
FIG. 5 is a perspective drawing of an embodiment of the present invention.

Referring to FIG. 5, in another embodiment, base (111) comprises a bracket (222) that includes a chinrest (333) and conveniently a forehead rest (444). For comfort and convenience, the bracket is adjustable to the subject's physiology (size, height, chin size, for example). Displacement sensor (456) is conveniently mounted on arm (555) effective to measure the area of interest (666) on the subject.

In another embodiment, the measurement apparatus of the present invention for measuring a metric of a measurement area of interest on a subject comprises an arm; a rest attached to or formed on the arm; a base attached to or formed on the arm; and a displacement sensor attached to the arm; wherein the arm, rest, and displacement sensor can be adjusted to optimize the spatial relationship between the displacement sensor and the measurement area of interest on the subject. In use, the apparatus is held by the measuring person at the base, the rest is placed on the subject, and the arm moved to optimize the displacement sensor's measurement of the measurement area of interest. Then the apparatus is held steady while measurement is made. Alternatively, the apparatus is held steady by the base, or the apparatus is placed on a steady surface by the base, and the subject is brought into contact with the rest and measurement is made. The rest can contact, for example, the subject's chin, forehead, or chest is measurement is desired of the throat area.

In another embodiment, the arm assembly comprises a multiplicity of arms with a multiplicity of locking joints convenient to allow a multiplicity of degrees of freedom for adjustment. After adjustment the locking joints are locked to hold the rest in steady alignment with the subject measurement area of interest and the displacement sensor. Thus, in use the subject places a convenient part of himself in contact with the rest (or, if more convenient, the rest is placed in contact with a part of the subject) and the displacement sensor is optimized in relation to the measurement area of interest by adjustment of the arms. The joints are then locked and measurement is made. The rest can conveniently be placed in contact with, for example, the chin, forehead, or chest.

In another embodiment, the arm assembly comprises a single arm that is conveniently sized and shaped to hold the rest at a location relative to the base for convenient measuring of the subject measurement area of interest. Thus, in use the subject places a convenient pat of himself in contact with the rest (or, if more convenient, the rest is placed in contact with a part of the subject) and the displacement sensor is optimized in relation to the measurement area of interest by movement of the single arm relative to the subject. The base can be held by hand by the measuring technician and measurement is made. The rest can conveniently be placed in contact with, for example, the chin, forehead, or chest. The rest and the base can be integral parts of the arm. The displacement sensor can be fixed to the arm or can be adjustably fixed to the arm, as convenient. It is preferred for there to be some adjustability to the attachment of the displacement sensor to the arm.

In another embodiment, the arm assembly comprises a multiplicity of springloaded frictionally held coiled segment (often called a "gooseneck" arm) conveniently to allow freedom for adjustment while having sufficient rigidity to maintain alignment for measurement. After adjustment, the gooseneck holds the rest in steady alignment with the subject measurement area of interest with the displacement sensor. Thus, in use the subject places a convenient part of himself in contact with the rest (or, if more convenient, the rest is placed in contact with a part of the subject) and the displacement sensor is optimized in relation to the measurement area of interest by adjustment of the gooseneck. The apparatus is held steady and measurement is made. The rest can conveniently be placed in contact with, for example, the chin, forehead, or chest.

In another embodiment, the base is formed in a portable case such as, for example, an attaché case into which the device conveniently collapses for easy transportation.

In another embodiment, an output port on the displacement sensor and a connecting cable allow the data from a performed measurement to be displayed on an external display such as, for example, a laptop computer that can also store and manipulate the data.

In another embodiment, the output data is formatted and broadcast for wireless reception to a handheld device for display/storage such as, for example, a PDA (personal digital assistant).

In use, in a method according to this invention, the subject is seated across a table from the therapist. The subject's chin is placed on the rest so that no movement other than the muscle movement of interest to the therapist (the measurement area of interest) is targeted by the displacement sensor. The rest keeps the measurement area of interest substantially still relative to the displacement sensor. Substantially still means that any movement is outside the temporal measurement regime so that such movement does not affect the accuracy of the measurement. Thus, in this embodiment the subject's chin is resting on the rest at an optimal distance from the displacement sensor (may be from about 1 inch to about 4 inches depending on the sensor design). The arm assembly is adjusted to assure comfort of the subject and the optimal relationship of the subject to the displacement sensor. The subject's external laryngeal/pharyngeal muscles are illuminated by the sensor beam and the subject is told to swallow. The displacement sensor measures and the device records the maximum amplitude movement of the muscle during the act of swallowing. The measurement may be repeated as needed to generate an average sample of the subject's ability to swallow. The data is displayed and may be transferred to a personal computer or PDA for inclusion in the subject's record and reviewed.

As described above, the subject can be in, for example, a chair or bed and the apparatus rest is brought into contact with the subject. The relationship of the displacement sensor to the measurement area of interest is optimized by movement and/or adjustment of the device of the invention and measurement is made with the device held steady. Alternatively, the subject can be in, for example, a chair or walker and the device mounted on a cart o table is brought to the subject. The device is adjusted to bring the rest in contact with the subject, the relationship of the displacement sensor to the subject measurement area of interest is optimized by movement and/or adjustment o the device, and measurement is made.

The measurement is repeated as needed over a period of time of therapy. When the measurements have reached the range of normal subjects, the therapy can be said to have been fully successful. Nevertheless, the chart of progress can show if the therapy is effective or some change in therapy might be needed as the subject may have reached a plateau of performance short of that of normal subjects.

As the device of this invention is portable and light, a therapist can transport it to subjects at various locations. Further, because the device of this invention allows for repeated measurements with precision independent of operator, such measurements can be performed by different people and still be compared to each other. Thus, savings may be had if less skilled workers can be used to make measurements that are then interpreted by more skilled personnel.

In an embodiment of this invention, the arm assembly is a box with the rest integrated into a side of the box. The rest and box are connected to one or two rod table top sliders and fastened with adjustable fasteners at the required height. Thus, the table top sliders and fasteners form the base. The rest and box move together as needed on the sliders to the required height. The displacement sensor is mounted inside the box and views the subject through a port in the box.

In another embodiment, the displacement sensor is a light-emitting-diode (LED) based sensor.

In another embodiment, the displacement sensor is a fiberoptic displacement sensor.

One skilled in the art readily understands the function of the aspects of the invention and the claims are not limited by the embodiments.

What I claim is:

1. A device for measuring a metric of a measurement area of interest on a subject comprising:
    an arm;
    a rest attached to or formed on the arm;
    a base attached to or formed on the arm; and
    a displacement sensor attached to the arm; wherein the arm, rest, and displacement sensor can be adjusted to maximize the spatial relationship between the displacement sensor and the measurement area of interest on the subject;
    wherein the metric is laryngeal or pharyngeal muscular movement upon swallowing.

2. The device according to claim 1, wherein the base is a clamping bracket.

3. The device according to claim 1, wherein the base comprises a storage case.

4. The device according to claim 1, wherein the displacement sensor is a laser measurement sensor.

5. The device according to claim 1, wherein the displacement sensor is a light emitting diode measurement sensor.

6. The device according to claim 1, wherein the displacement sensor is a fiberoptic displacement sensor.

7. The device according to claim 1, wherein the displacement sensor sends its output to a computer, or handheld portable data device or a PDA.

8. A device for measuring a metric of a measurement area of interest on a subject comprising:
    a base;
    an arm assembly lockably adjustably connected to the base;
    a rest lockably adjustably connected to the arm assembly; and
    a displacement sensor lockably adjustably attached to the arm assembly; wherein the arm, rest, and displacement sensor can be adjusted to maximize the spatial relationship between the displacement sensor and the measurement area of interest on the subject and locked in such relationship;
    wherein the metric is laryngeal or pharyngeal muscular movement upon swallowing.

9. The device according to claim 8, wherein the arm assembly comprises a multitude of arms and lockable adjustable joints.

10. The device according to claim 8, wherein the base is a clamping bracket.

11. The device according to claim 8, wherein the base comprises a storage case.

12. The device according to claim 8, wherein the displacement sensor is a laser measurement sensor.

13. The device according to claim 8, wherein the displacement sensor is a light emitting diode measurement sensor.

14. The device according to claim 8, wherein the displacement sensor sends its output to a computer, or handheld portable data device or a PDA.

15. A method of measuring a metric of a measurement area of interest on a subject comprising:
    contacting a part of the subject on a rest of a measurement apparatus that comprises an arm, a base attached to or formed on the arm, a rest attached to or formed on the arm, and a displacement sensor attached to the arm;
    adjusting the measurement apparatus to maximize the spatial relationship between the displacement sensor and the measurement area of interest on the subject; and
    measuring the metric;
    wherein the metric is laryngeal or pharyngeal muscular movement upon swallowing.

16. A method of measuring a metric of a measurement area of interest on a subject comprising:
    placing a part of the subject on a rest of a measurement apparatus that comprises a base, an arm assembly lockably adjustably connected to the base, a rest adjustably lockably connected to the arm assembly, and a displacement sensor lockably adjustably attached to the arm assembly;
    adjusting the measurement apparatus to maximize the spatial relationship between the displacement sensor and the measurement area of interest on the subject;
    locking the measurement apparatus in such relationship; and
    measuring the metric;
    wherein the metric is laryngeal or pharyngeal muscular movement upon swallowing.

* * * * *